(12) United States Patent
Lai et al.

(10) Patent No.: US 8,900,547 B2
(45) Date of Patent: Dec. 2, 2014

(54) SYNTHESIS OF HIGH ACTIVITY LARGE CRYSTAL ZSM-5

(71) Applicant: ExxonMobil Research and Engineering Company, Annandale, NJ (US)

(72) Inventors: Wenyih Frank Lai, Bridgewater, NJ (US); Merci A. Hamilton, Easton, PA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 242 days.

(21) Appl. No.: 13/685,794

(22) Filed: Nov. 27, 2012

(65) Prior Publication Data
US 2013/0144100 A1    Jun. 6, 2013

Related U.S. Application Data

(60) Provisional application No. 61/565,635, filed on Dec. 1, 2011.

(51) Int. Cl.
| | |
|---|---|
| *C01B 39/38* | (2006.01) |
| *B01J 29/40* | (2006.01) |
| *B01J 35/02* | (2006.01) |
| *C07C 6/12* | (2006.01) |

(52) U.S. Cl.
CPC .............. *B01J 29/40* (2013.01); *C01B 39/38* (2013.01); *B01J 35/023* (2013.01); *C07C 6/123* (2013.01); *B01J 2229/123* (2013.01); *B01J 2229/32* (2013.01); *C07C 2529/40* (2013.01)
USPC ......................................... 423/701; 423/702

(58) Field of Classification Search
CPC ......... C01B 39/38; B01J 29/40; B01J 35/023; B01J 2229/32; B01J 2229/123; C07C 6/123; C07C 2529/40
USPC .................................................. 423/701, 702
See application file for complete search history.

(56) References Cited

U.S. PATENT DOCUMENTS

| | | | |
|---|---|---|---|
| 3,354,078 A | 11/1967 | Miale et al. | |
| 3,676,063 A * | 7/1972 | Elo et al. | ........................ 423/701 |
| 3,702,886 A | 11/1972 | Argauer et al. | |
| 4,088,605 A | 5/1978 | Rollmann | |
| 4,797,267 A * | 1/1989 | Kuehl | ........................... 423/704 |
| 6,013,239 A | 1/2000 | Chen et al. | |
| 2002/0011429 A1 * | 1/2002 | Iino et al. | .................. 208/111.35 |
| 2003/0003035 A1 * | 1/2003 | Stamires et al. | .............. 422/225 |
| 2006/0111234 A1 | 5/2006 | Kim et al. | |

FOREIGN PATENT DOCUMENTS

| | | |
|---|---|---|
| EP | 21674 A1 | 1/1981 |
| WO | 2009103394 A2 | 8/2009 |

OTHER PUBLICATIONS

Weisz et al., "Superactive Crystalline Aluminosilicate Hydrocarbon Catalysts", Journal of Catalysis, 4, pp. 527, (1965).
Miale et al., "Catalysis by Crystalline Aluminosilicates, IV. Attainable Catalytic Cracking Rate Constants, and Superactivity", Journal of Catalysis, 6, pp. 278, (1966).
Olson et al., "Chemical and Physical Properties of the ZSM-5 Substitutional Series", Journal of Catalysis, 61, pp. 395, (1980).
International Search Report and Written Opinion from PCT/US2012/066588 dated Nov. 27, 2012.

* cited by examiner

*Primary Examiner* — David M Brunsman
(74) *Attorney, Agent, or Firm* — David M. Weisberg (57) ABSTRACT

In a process for preparing a high activity, large crystal ZSM-5 type zeolite in the absence of a template, a reaction mixture can be prepared comprising water, a silica source having a surface area less than 150 $m^2/g$, an alumina source, seeds, a source of an oxide of an alkali metal, M, and a source of gluconic acid or salt thereof, Q, wherein the mixture has a $SiO_2/Al_2O_3$ molar ratio $\leq 40$. The reaction mixture can be heated to a crystallization temperature from about 100° C. to 200° C. for a time sufficient for crystals of ZSM-5 to form Crystals of ZSM-5 can then be recovered from the reaction mixture which crystals can have a $SiO_2/Al_2O_3$ molar ratio $\leq 40$ and a majority of which crystals can have at least one crystalline dimension of at least about 2 μm.

8 Claims, 4 Drawing Sheets

SYNTHESIS OF HIGH ACTIVITY LARGE CRYSTAL ZSM-5

CROSS-REFERENCE TO RELATED APPLICATIONS

This application claims the benefit of U.S. Provisional Application Ser. No. 61/565,635, filed on Dec. 1, 2011, the contents of which are hereby incorporated by reference in their entirety.

FIELD O THE INVENTION

This invention relates to a method for preparing relatively high activity, relatively large crystal ZSM-5 use a template-free synthesis system.

BACKGROUND OF THE INVENTION

ZSM-5 crystalline aluminosilicate zeolites and methods for preparing ZMS-5 are known. For example. U.S. Pat. No. 3,702,886, the entire contents of which are incorporated herein by reference, discloses a process for preparing ZSM-5 using a mixture of alkali metal cations and tetraalkylammonium cations, such as tetrapropylammonium (TPA) cations. In this process, the tetraalkylammonium cations are believed to act as a template to direct the synthesis of the ZSM-5 structure so that the resultant zeolite contains the template within its pore structure.

European Patent No. EP-A-21674 teaches that large crystal ZSM-5, having a crystal size in excess of 1 micron, can be prepared from a reaction mixture containing TPA cations, provided that the OH—/$SiO_2$ ratio is maintained within the range from 0.01-0.07.

Relatively large crystal ZSM-5 (>1 micron) usually can be prepared without difficulty when the aluminum content in the synthesis mixture is low. As a result, with large crystal ZSM-5, although $SiO_2/Al_2O_3$ molar ratios of 100 or higher are relatively easily attainable, $SiO_2/Al_2O_3$ molar ratios of 40 or lower are typically rather difficult to attain.

Catalysts prepared from ZMS-5 crystals of medium (about 0.5 micron in size) and especially large (greater than about 1 micron in size) size and high activity (low $SiO_2/Al_2O_3$ molar ratio) can be useful in, for example, selective toluene disproportionation to produce para-xylene, an aromatic raw material that can be used to make polyethylene terephthalate (PET).

U.S. Pat. No. 6,013,239, the entire contents of which are incorporated herein by reference, discloses a method of preparing large crystal ZSM-5 (of the order of 3 microns) with high aluminum content ($SiO_2/Al_2O_3$=25-40), but only in the presence of amino acids. Examples of suitable amino acids are said to include 6-aminohexanoic acid, N-2-adamantylglycine, N-cyclohexylglycine, lysine, and glutamic acid (and its monosodium salt). The amino acids are believed to act as nucleation suppressing agents rather than templates or structure directing agents, since the amino acids do not appear to become entrained in the pore structure of the resultant zeolite. However, attempts to scale-up this process have to date proved unsuccessful, since, due to the high viscosity of the synthesis gel, it has not been possible to reproduce the large crystal size materials in relatively larger scale batches.

According to the invention, it has now been found that by using relatively low surface area (<150 in/g) silica sources in combination with specific nucleation suppressors in the synthesis gel, it is possible to produce ZSM-5 having a relatively large crystal size (≥about 2 microns) and a relatively high alumina content ($SiO_2/Al_2O_3$ molar ratio of 40 or lower). In addition, the reaction gels produced using these new formulations have been found to be functional at lower viscosities than those employing conventional silica sources, making the process more readily amenable to larger scale syntheses.

U.S. Pat. No. 4,088,605 discloses a method of synthesizing a crystalline aluminosilicate zeolite, such as ZSM-5, having an aluminum-free outer shell of $SiO_2$, said zeolite being made by a two stage method comprising (i) initiating crystallization in a crystallization medium to produce the zeolite, and (ii) then altering the crystallization medium to substantially eliminate the aluminum therein, for example, by adding a complexing agent for the aluminum selected from the group consisting of gluconic acid, tartaric acid, nitrilotriacetic acid and ethylenediaminetetraacetic acid. There is no disclosure or suggestion in the '605 patent that, by adding the aluminum complexing agent at the initiation of the synthesis, it would be possible to produce large crystal ZSM-5 with a uniformly high aluminum content, and hence activity.

SUMMARY OF THE INVENTION

In one aspect, the invention can reside in a process for preparing a high activity, large crystal ZSM-5 type zeolite in the absence of a template, the process comprising: (a) preparing a reaction mixture comprising water, a silica source having a surface area less than 150 $m^2$/g, an alumina source, seeds, a source of an oxide of an alkali metal, M, and a source of gluconic acid or salt thereof, Q, wherein said mixture can have a $SiO_2/Al_2O_3$ molar ratio≤40, e.g., from about 15 to 40, and optionally also a viscosity at ~25° C. of less than 1000 cP; (b) heating the reaction mixture to a crystallization temperature from about 100° C. to 200° C. for a time sufficient for crystals of ZSM-5 to form, e.g., from about 2 hours to about 100 hours or from about 10 hours to about 100 hours; and (c) recovering from the reaction mixture crystals of ZSM-5 having a $SiO_2/Al_2O_3$ molar ratio≤40 (e.g., from about 15 to 40), wherein a majority of the crystals have at least one crystalline dimension of at least about 2 μm.

In certain embodiments, the reaction mixture can have one or more of the following molar composition characteristics: $SiO_2/Al_2O_3$ of up to about 40/1, e.g., from about 15/1 to about 40/1; $H_2O/SiO_2$ from about 5 to about 50; $OH^-/SiO_2$ from about 0.05 to about 0.5; $M/SiO_2$ from about 0.05 to about 0.5; and $Q/SiO_2$ from about 0.05 to about 1.0.

Additionally or alternately, the seeds in the reaction mixture comprise or be ZSM-5 seeds from a previous synthesis, typically in an amount between about 50 wppm and 50000 wppm of the reaction mixture. Further additionally or alternately, the ZSM-5 recovered in step (c) can have an alpha value, in its hydrogen form, of at least 1000.

In further aspects, the invention can reside in ZSM-5 produced by the process described herein and/or in the use of an active and silicon-selectivated form of the ZSM-5 in a process for selectively disproportionating toluene to para-xylene.

DETAILED DESCRIPTION OF THE EMBODIMENTS

As taught by U.S. Pat. Nos. 3,702,886 and RE 29,948, ZSM-5 can have an XRD (X-ray diffraction) pattern including the characteristic lines listed in Table 1 below:

TABLE 1

| Interplanar d-Spacing (Å) | Relative Intensity (100*I/$I_o$) |
|---|---|
| 11.00 ± 0.25 | s-vs |
| 9.80 ± 0.30 | m-vs |
| 6.70 ± 0.10 | w |
| 6.30 ± 0.10 | w |
| 5.98 ± 0.10 | w |
| 5.55 ± 0.10 | w |
| 5.00 ± 0.10 | w |
| 4.36 ± 0.10 | w |
| 4.25 ± 0.08 | w |
| 4.08 ± 0.05 | w |
| 3.85 ± 0.07 | m-vs |
| 3.71 ± 0.05 | w-m |
| 3.62 ± 0.04 | w |
| 3.04 ± 0.03 | w |
| 2.99 ± 0.02 | w |

The XRD data reported herein were collected with a D4 Endeaver diffraction system from Bruker Corporation, equipped with a germanium solid state detector, using copper K-alpha radiation. The diffraction data were recorded by step-scanning at ~0.02° two-theta, where theta is the Bragg angle, and a counting time of ~10 seconds for each step. The interplanar spacings, d-spacings, were calculated in Angstrom units, and the relative intensities of the lines, I/$I_o$ (expressed in hundredths of the intensity of the strongest line, above background), were derived with the use of a profile fitting routine (or using a second derivative algorithm). The intensities disclosed herein are uncorrected for Lorentz and polarization effects, unless otherwise noted. The relative intensities are given in terms of the symbols: vs=very strong (~75-100), s=strong (~50-74), m=medium (~25-49) and w=weak (~0-24).

Describe herein is a process for the synthesis of ZSM-5 crystals laving a $SiO_2/Al_2O_3$ molar ratio≤40, e.g., from about 15 to about 40 or from about 15 to about 35, wherein a majority of the crystals have at least one crystalline dimension (e.g., for roughly uniform particles, such as spherical, regular octagonal, regular hexagonal, and/or square, a diameter or effective diameter; for roughly elongated particles, including elliptical, cylindrical, prismatic, pyramidal, plate-like, discotic, and/or the like, a major dimension, or both a major dimension and at least one minor dimension) of at least about 2 μm. By virtue of its relatively low $SiO_2/Al_2O_3$ molar ratio, the ZSM-5 produced by the present process can also be characterized as exhibiting a relatively high acid activity. Acid activity can be conveniently measured by the Alpha test, in which the acid activity of a zeolite catalyst is compared with a standard silica-alumina catalyst. The alpha test is described in U.S. Pat. No. 3,354,078; in the Journal of Catalysis, v. 4, p. 527 (1965); v. 6, p. 278 (1966); and v. 61, p. 395 (1980), each of which is incorporated herein by reference as to that description. The experimental conditions of the test used herein include a constant temperature of ~538° C. and a variable flow rate as described in detail in the Journal of Catalysis, v. 61, p. 395. The higher alpha values tend to correspond with a relatively more active catalyst. Typically, the ZSM-5 produced by the present process has an Alpha value of at least 1000, e.g., of at least 1500.

In the present process, ZSM-5 can be synthesized from a reaction mixture comprising water, a silica source having a surface area less than 150 m²/g, an alumina source, a source of an oxide of an alkali metal, M, seeds such as ZSM-5 seeds, and a nucleation suppressor, Q, selected from gluconic acid, triethanolamine, nitrilotriacetic acid, ethylene-diaminetetraacetic acid, and salts thereof, wherein the mixture has a composition, in terms of mole ratios of oxides, within one or more of the following ranges:

| Reactants | Useful | Preferred |
|---|---|---|
| $SiO_2/Al_2O_3$ | up to ~40 | ~15 to ~40 |
| $H_2O/SiO_2$ | ~5 to ~50 | ~10 to ~20 |
| $OH^-/SiO_2$ | ~0.05 to ~0.5 | ~0.15 to ~0.4 |
| $M/SiO_2$ | ~0.05 to ~0.5 | ~0.15 to ~0.4 |
| $Q/SiO_2$ | ~0.05 to ~1.0 | ~0.1 to ~0.5 |

Suitable sources of silica can include, but are not necessarily limited to, colloidal suspensions of silica, precipitated silica, alkali metal silicates, tetraalkyl orthosilicates, and the like, as well as combinations thereof. Suitable sources of aluminum can include, but are not necessarily limited to, hydrated alumina, water-soluble aluminum salts such as aluminum nitrate and/or sodium aluminate, and the like, as well as combinations thereof.

The reaction mixture can also comprise zeolite seeds, particularly ZSM-5 seeds such as from a previous ZSM-5 synthesis, which seeds can typically be present in an amount between about 50 wppm and 50,000 wppm of the overall reaction mixture.

In some preferred embodiments, the final reaction mixture can have a viscosity at ~25° C. of less than 1000 cP, e.g., less than 800 cP.

Crystallization of ZSM-5 from the reaction mixtures disclosed herein can be carried out at either static or (in some preferred embodiments) stirred conditions in a suitable reactor vessel, for example, in polypropylene jars, in Teflon®-lined or stainless steel autoclaves, or the like, at a temperature from about 100° C. to about 200° C. for a time sufficient for crystallization to occur at the temperature used, e.g., from about 2 hours to about 100 hours or from about 10 hours to about 100 hours. Thereafter, the crystals can be recovered, e.g., by separation from the liquid.

To the extent desired and depending on the $X_2O_3/YO_2$ molar ratio of the material, any alkali and/or alkaline earth metal cations in the as-synthesized ZSM-5 can be replaced in accordance with techniques well known in the art (e.g. by ion exchange with other cations). Preferred replacing cations can, in some embodiments, include metal ions, hydrogen ions, hydrogen precursor (e.g., ammonium ions), and combinations thereof. Particularly preferred cations can be those that can facilitate tailoring of the catalytic activity of the resulting catalyst composition for certain hydrocarbon conversion reactions, which can include, but are not necessarily limited to, hydrogen, rare earth metals, metals of Groups 2 to 15 of the Periodic Table of the Elements, and combinations thereof. As used herein, the numbering scheme for the Groups of the Periodic Table of the Elements is as disclosed in Chemical and Engineering News, 63(5), 27 (1985).

The as-synthesized ZSM-5 may also be subjected to treatment to remove part or all of the nucleation suppressor Q used in its synthesis. This can conveniently be effected by thermal treatment, e.g., by heating the as-synthesized material to a temperature of at least about 370° C. for at least 1 minute (e.g., generally not longer than about 20 hours). While subatmospheric or superatmospheric pressure can be employed for the thermal treatment, roughly atmospheric pressure can typically be desirable for reasons of convenience. The thermal treatment can be performed at a temperature up to about 925° C. The thermally treated product, especially in its metal, hydrogen, and/or ammonium forms, can be particularly useful in the catalysis of certain organic (e.g., hydrocarbon) conversion reactions.

The ZSM-5 material may, in certain embodiments, be intimately combined with a hydrogenating component, such as containing molybdenum, rhenium, nickel, cobalt, chromium, manganese, and/or a noble metal such as platinum and/or palladium, where a hydrogenation-dehydrogenation function is desired to be performed. Such component can be in the composition, for instance, by way of co-crystallization, exchanged into the composition (to the extent a Group IIIA element, such as aluminum, is present in the structure), impregnated therein, and/or intimately physically admixed therewith. Such component can be impregnated into/onto it, for example, in the case of platinum, by treating the silicate with a solution containing a platinum metal-containing ion. Thus, suitable platinum compounds for this purpose can include, but are not necessarily limited to, chloroplatinic acid, platinous chloride, and/or various compounds containing a platinum-amine complex.

The ZSM-5 material, when employed as an adsorbent and/or as a catalyst, can generally be at least partially dehydrated, e.g., by heating to a temperature in the range from about 200° C. to about 370° C., for instance, in an atmosphere such as air, nitrogen, etc., and at atmospheric, subatmospheric, or superatmospheric pressures for an appropriate time (such as between about 30 minutes and about 48 hours). Dehydration can additionally or alternately be performed at room temperature merely by placing the ZSM-5 in a vacuum, but a longer time may be required to obtain a sufficient amount of dehydration.

The ZSM-5 described herein can be used as an adsorbent and/or as a catalyst for a wide variety of organic compound conversion processes, including many of present commercial/industrial importance. Examples of chemical conversion processes that can be effectively catalyzed by the ZSM-5 described herein can advantageously include those where relatively high acid activity and relatively large crystal size are important, such as toluene disproportionation.

As in the case of many catalysts, it may be desirable to incorporate the ZSM-5 material with another material resistant to the temperatures and other conditions employed in organic conversion processes. Such materials can include active and/or inactive materials, synthetic and/or naturally occurring zeolites, inorganic materials such as clays, silica, and/or other metal oxides such as alumina, and the like, and combinations thereof. The latter inorganic materials may be naturally occurring and/or in the form of gelatinous precipitates (gels) including mixtures of silica and optionally other metal oxides. Use of a material in conjunction with an active/activated form of the ZSM-5 material described herein (i.e., combined therewith and/or present during synthesis of the new crystal) can sometimes change the conversion rate and/or selectivity of the ZSM-5-containing catalyst in certain organic conversion processes, Inactive materials can suitably serve as diluents, e.g., to control the amount of conversion in a given process so that products can be obtained in an economic and orderly manner, for instance without employing other means for controlling the rate of reaction. These materials may be incorporated into naturally occurring clays, e.g., bentonite and/or kaolin, to improve the crush strength of the catalyst under commercial operating conditions. Said materials (such as clays, oxides, etc.) can function as binders for the ZSM-5-containing catalyst. It can be desirable to provide a catalyst having good crush strength, because, in commercial use, it can generally be desirable to prevent the catalyst from breaking down into powder-like materials. Such clay and/or oxide binders can normally be employed primarily (only) for the purpose of improving the crush strength of the catalyst.

Naturally occurring clays which can be composited with the ZSM-5 material described herein can include, but are not necessarily limited to, the montrnorillonite and kaolin familis, including the subbentonites and the kaolins commonly known as Dixie, McNamee, Georgia and Florida clays, or others in which the main mineral constituent is halloysite, kaolinite, dickite, nacrite, and/or anauxite. Such clays can be used in their raw state (as originally mined) and/or as initially subjected to calcination, acid treatment, and/or chemical modification. Binders useful for compositing with ZSM-5 can additionally o alternately include inorganic oxides, such as silica, zirconia, titania, magnesia, beryllia, alumina, and mixtures thereof.

In addition to the foregoing materials, the ZSM-5 material described herein can be composited with a porous matrix material, e.g., silica-alumina, silica-magnesia, silica-zirconia, silica-thoria, silica-beryllia, silica-titania, including ternary compositions such as silica-alumina-thoria, silica-alumina-zirconia, silica-alumina-magnesia, and silica-magnesia-zirconia, as well as combinations and/or composites thereof.

When present, the relative proportions of ZSM-5 and inorganic oxide matrix may vary widely, with the ZSM-5 content capable of ranging from about 1 wt % to about 90 wt %, or, particularly in bead form composite preparations, ranging from about 2 wt % to about 80 wt %. Routinely, but not uniformly, the ZSM-5 content can be at least 25 wt %, e.g., at least 30 wt %; at least 35 wt %; at least 40 wt %, at least 45 wt %, at least 50 wt %, at least 60 wt %, or at least 75 wt %.

In certain embodiments, the ZSM-5 produced by the present process can be intended for use as a catalyst in the selective disproportionation of toluene to para-xylene. In such an application, the ZSM-5, in either bound or unbound form, can be initially subjected to multiple stages of silicon selectivation. Each silicon selectivation stage can involve impregnating the catalyst with one or more silicon compound, normally an organosilicon compound, in a carrier liquid, followed by one or more calcination steps to remove the carrier liquid and ultimately to convert the (organo)silicon compound(s) to silica.

Useful selectivating agents can include, but are not limited to, siloxanes that can be characterized by the general formula:

where each $R_1$ and $R_2$ are independently selected from hydrogen, halogen, hydroxyl, alkyl, halogenated alkyl, aryl, halogenated aryl, aralkyl, halogenated aralkyl, alkaryl, or halogenated alkaryl, and where n is an integer of at least 2 and generally from 3 to 1000 or from 5 to 900. The hydrocarbon substituents in the $R_1$ and $R_2$ groups can generally contain from 1 to 10 carbon atoms each (e.g., methyl-, ethyl-, and/or phenyl-containing groups can be preferred in certain embodiments). The (number average) molecular weight of the siloxanes employed can generally be between about 80 g/mol and about 20,000 g/mol (e.g., from about 150 g/mol to about 10,000 g/mol). Representative siloxanes can include, but are not limited to, dimethyl silicone, diethyl silicone, phenylmethyl silicone, methylhydrogen-silicone, ethylhydrozen silicone, phenylhydrogen silicone, methylethyl silicone, phenylethyl silicone, diphenyl silicone, methyltrithoropropyl silicone, ethyltri-fluoroproply silicone, polydimethyl silicone, tetrachloro-phenyl methyl silicone, tetrachlorophenylethyl tetrachlorophenylhydrogen silicone, tetrachlorophenylphenyl silicone, methylvinyl silicone, ethylvinyl silicone, and the like, and combinations and/or copolymers thereof. The siloxane compound(s) need not be linear, and may be branched and/or cyclic (for example, hexamethyl cyclotrisiloxane, octamethyl cyclo-tetrasiloxane, hexaphenyl cyclotrisiloxane, octaphenyl cyclotetrasiloxane, and the like, and combinations thereof). Mixtures of these compounds may additionally or alternately be used, as may siloxanes/silicones with other functional groups.

Preferably, the kinetic diameter of the para-selectivating agent can be larger than the zeolite pore diameter, in order to inhibit/reduce/prevent (a) entry of the selectivating agent into the zeolite pores and/or (b) concomitant reduction in the internal activity of the catalyst. Preferred silicon-containing selectivating agents can include, but are not limited to, dimethylphenylmethyl polysiloxane (e.g., Dow-550™) and/or phenylmethyl polysiloxane (e.g., Dow-710™). Dow-550™ and Dow-710™ can be commercially obtained from Dow Chemical Co., Midland, Mich.

Examples of suitable organic carriers for the selectivating agent can include hydrocarbons such as linear, branched, and/or cyclic alkanes having five or more carbons. In certain methods of the present invention, it can be preferable for the carrier to comprise or be a linear, branched, and/or cyclic alkane having a boiling point greater than about 70° C. and also containing 6 or more carbons. Optionally, mixtures of low volatility organic compounds, such as hydrocracker recycle oil, may additionally or alternately be employed as carriers. Particular low volatility hydrocarbon carriers of selectivating agents can include decane and/or dodecane.

The ZSM-5 catalyst may be modified, post-synthesis and/or post-formulation, in order to reduce the amount of undesirable by-products (particularly ethylbenzene) produced in the toluene disproportionation process. Such modification can typically involve incorporating a hydrogenation/dehydrogenation function within the catalyst composition, such as by addition of a metal compound such as containing platinum. While platinum is a preferred metal, other metals of Groups IB to VIIIB of the Periodic Table of Elements may additionally or alternately be utilized, e.g., palladium, nickel, copper, cobalt, molybdenum, rhodium, ruthenium, silver, gold, mercury, osmium, iron, zinc, cadmium, and mixtures thereof. The modification metal may be added, e.g., by cation exchange, in amounts from about 0.001 wt % to about 2 wt %, typically from about 0.3 wt % to about 1 wt % or from about 0.4 wt % to about 0.7 wt %. For example, a platinum modified ZSM-5 catalyst can be prepared by first adding the catalyst to a solution of ammonium nitrate in order to convert the catalyst to the ammonium form. The catalyst can subsequently be contacted with an aqueous solution of tetraamine platinum (II) nitrate and/or tetraamine platinum(II) chloride. The catalyst can then be filtered, washed with water, and calcined at an appropriate temperature, e.g., from about 250° C. to about 500° C. The metal modification may be conducted before or after the selectivation process.

In toluene disproportionation applications, the selectivated and optionally metal modified catalyst can then contacted with toluene, normally in the presence of hydrogen, under disproportionation conditions, which can include one or more of a reactor inlet temperature from about 200° C. to about 500° C. (e.g., from 350° C. to about 500° C.), a reactor pressure from about atmospheric pressure (about 15 psia; or about 100 kPaa) to about 5000 psia (about 34 MPaa), e.g., from about 100 psia (about 690 kPaa) to about 1000 psia (about 6.9 MPaa); a weight hourly space velocity (WHSV) from about 0.1 hr$^{-1}$ to about 20 hr$^{-1}$, e.g., from about 2 hr$^{-1}$ to about 10 hr$^{-1}$; and a H$_2$/hydrocarbon molar ratio from about 0.1 to about 20, e.g., from about 1 to about 10.

The invention will now be more particularly described with reference to the following non-limiting Examples and the accompanying drawings.

EXAMPLES

Example 1

Comparative

ZSM-5 crystals were synthesized from a reaction mixture comprising Sipernat®-320 silica, aluminum sulfate, NaOH, and deionized water in amounts sufficient to provide the following molar composition:

| | |
|---|---|
| SiO$_2$/Al$_2$O$_3$ | ~40 |
| H$_2$O/SiO$_2$ | ~13.9 |
| OH$^-$/SiO$_2$ | ~0.27 |

Sipernat®-320 is a form of precipitated silica having a surface area of about 175 m$^2$/g and is commercially available from Evonik Degussa GmbH.

Figure 1:
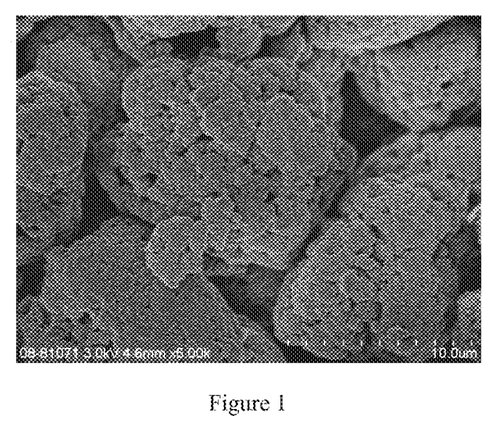
FIG. 1 provides a scanning electron microscope (SEM) image of the product of Comparative Example 1.

The reaction mixture was heated to about 320° F. (about 160° C.) for about 24 hours, and as-synthesized ZSM-5 crystals were then isolated therefrom. The SEM of the as-synthesized material showed agglomerates of medium-sized crystals (about 0.5 µm and smaller), as shown in FIG. 1. The as-synthesized ZSM-5 crystals exhibited a SiO$_2$/Al$_2$O$_3$ molar ratio of about 25.

Examples 2A and 2B

A mixture was prepared from ~950 grams ater, ~270 grams of Sipernat®-120 or -350, respectively, ~40 grams of sodium aluminate solution (45% in water and ~69 grams of 50% aqueous sodium hydroxide solution. Then ~9 grams of ZSM-5 seeds were added to the mixture. The mixture exhibited the following molar composition:

| | |
|---|---|
| SiO$_2$/Al$_2$O$_3$ | ~40 |
| H$_2$O/SiO$_2$ | ~13.9 |
| OH$^-$/SiO$_2$ | ~0.27 |

Sipernat®-120 and -350 are forms of precipitated silica having surface areas of about 120 m$^2$/g and less than 100 m$^2$/g, respectively, and are commercially available from Evonik Degussa GmbH.

Figure 2A:
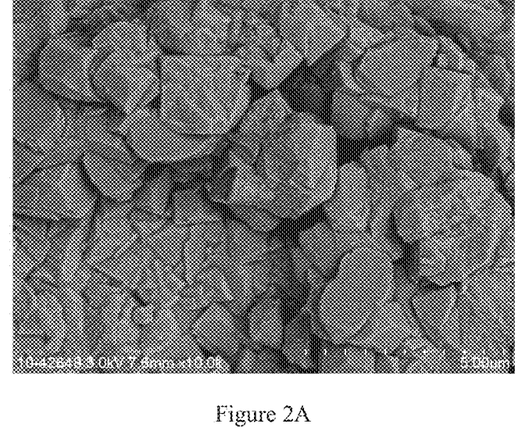
FIGS. 2A and 2B provide SEM images of the products of Example 2A and 2B, respectively.
Figure 2B:
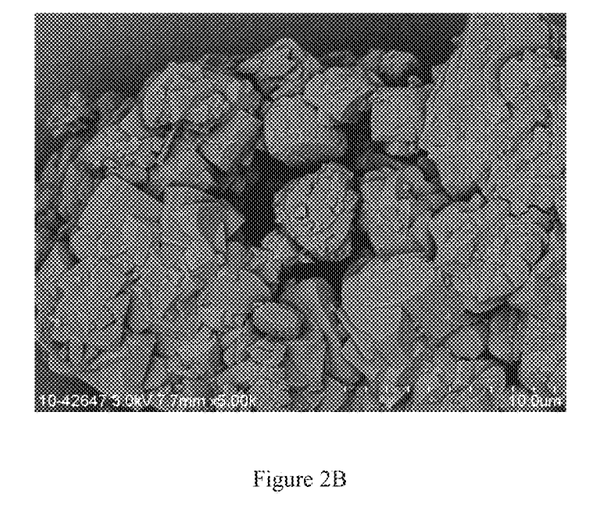

Each reaction mixture was heated to about 320° F. (about 60° C.) in a ~2-liter autoclave with stirring at approximately 250 rpm for about 36 hours. Each product was filtered, washed with deionized (DI) water, and dried at ~250° F. (~120° C.). The XRD patterns of each as-synthesized material showed the typical phase of ZSM-5 topology. The SEM of each as-synthesized material evidenced relatively large crystals, with an average size of about 1 to 4 microns, as shown in FIGS. 2A and 2B, respectively. The as-synthesized ZSM-5 crystals exhibited a $SiO_2/Al_2O_3$ molar ratio of about 29.6 (2A) and about 26.1 (2B).

Example 3

A mixture was prepared from ~950 grams of water, ~273 grams of Sipernat®-120, ~45 grams of sodium aluminate solution (45% in water), ~89 grams of triethanolamine (TEA) solution (98%), and ~69 grams of 50% aqueous sodium hydroxide solution. Then ~9 grams of ZSM-5 seeds were added to the mixture. The mixture exhibited the following molar composition:

| | |
|---|---|
| $SiO_2/Al_2O_3$ | ~36 |
| $H_2O/SiO_2$ | ~13.9 |
| $OH^-/SiO_2$ | ~0.29 |
| $Na^+/SiO_2$ | ~0.29 |

Figure 3:
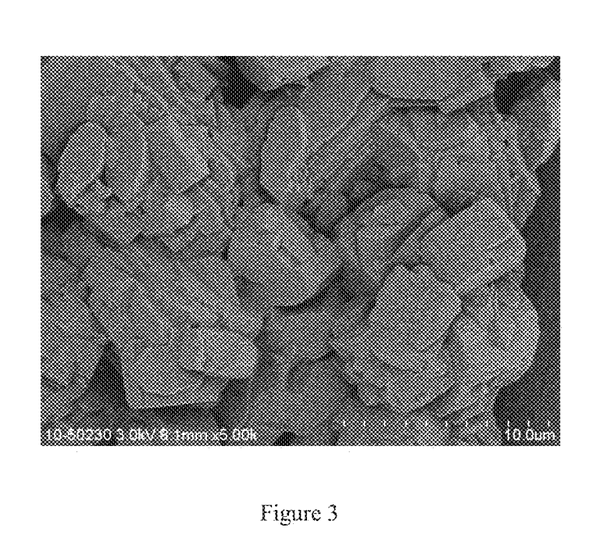
FIG. 3 provides an SEM image of the product of Example 3.

The reaction mixture was heated to about 320° F. (about 160° C.) in a ~2-liter autoclave with stirring at approximately 250 rpm for about 36 hours. The product was filtered, washed with deionized (DI) water, and dried at ~250° F. (~120° C.). The XRD pattern of the as-synthesized material showed the typical phase of ZSM-5 topology. The SEM of the as-synthesized material evidenced more uniform large crystals than those obtained in Example 2, with an average size of about 3 microns, as shown in FIG. 3. The as-synthesized ZSM-5 crystals exhibited a $SiO_2/Al_2O_3$ molar ratio of about 25. H-form crystals were produced by three separate treatments of ion-exchange with ~1N ammonium hydroxide solution (in water), followed by calcination at about 540° C. for ~4 hours, and were characterized by an Alpha value of ~3,300 and a surface area of ~430 m²/g (~425 m²/g in microporous SA+~5 m²/g in mesoporous SA).

Example 4

A mixture was prepared from ~950 grams of water, ~270 grams of Sipernat®-120, ~40 grams of sodium aluminate solution (45% in water), ~43 grams of d-gluconic acid monosodium salt, and ~69 grams of 50% aqueous sodium hydroxide solution. Then ~9 grams of ZSM-5 seeds were added to the mixture. The mixture exhibited the following molar composition:

| | |
|---|---|
| $SiO_2/Al_2O_3$ | ~40 |
| $H_2O/SiO_2$ | ~13.9 |
| $OH^-/SiO_2$ | ~0.27 |

Figure 4:
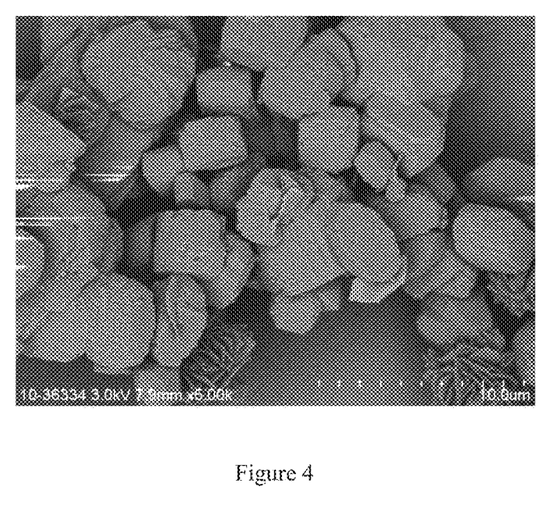
FIG. 4 provides an SEM image of the product of Example 4.

The reaction mixture was heated to about 320° F. (about 160° C.) in a ~2-liter autoclave with stirring at approximately 250 rpm for about 36 hours. The product was filtered, washed with deionized (DI) water, and dried at ~250° F. (~120° C.). The mother liquor showed a dark brown color after filtration. The XRD pattern of the as-synthesized material showed the typical phase of ZSM-5 topology. The SEM of the as-synthesized material evidenced more uniform large crystals than those obtained in Example 2, with an average size of about 3 microns, as shown in FIG. 4. The as-synthesized ZSM-5 crystals exhibited a $SiO_2/Al_2O_3$ molar ratio of about 33. H-form crystals were produced by three separate treatments of ion-exchange with ~1N ammonium hydroxide solution (in water), followed by calcination at about 540° C. for ~4 hours, and were characterized by an Alpha value of ~1,700 and a surface area of ~422 m²/g (~414 m²/g in microporous SA+~8 m²/g in mesoporous SA).

Example 5

A mixture was prepared from ~9.5 kg of water, ~2.7 kg of Sipernat®-120, ~400 grams of sodium aluminate solution (45% in water), ~430 grams of d-gluconic acid monosodium salt, and ~690 grams of 50% aqueous sodium hydroxide solution. Then ~20 grams of ZSM-5 seeds were added to the mixture. The mixture exhibited the following molar composition:

| | |
|---|---|
| $SiO_2/Al_2O_3$ | ~40 |
| $H_2O/SiO_2$ | ~13.9 |
| $OH^-/SiO_2$ | ~0.27 |

Figure 5:
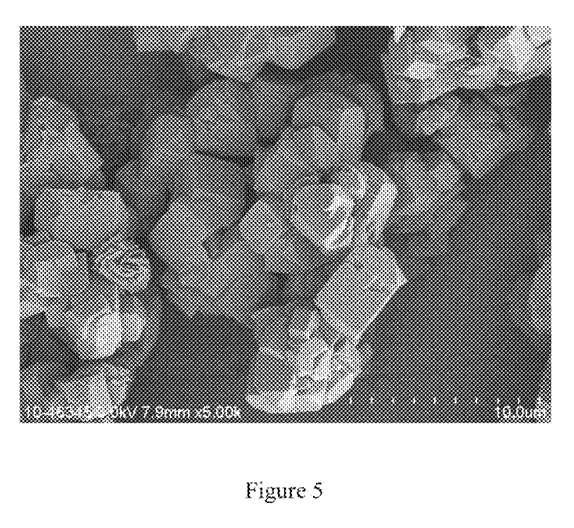
FIG. 5 provides an SEM image of the product of Example 5.

The reaction mixture was heated to about 320° F. (about 160° C.) in a ~5-gallon autoclave with stirring at approximately 60 rpm for about 36 hours. The product was filtered, washed with deionized (DI) water, and dried at ~250° F. (~120° C.). The XRD pattern of the as-synthesized material showed the typical phase of ZSM-5 topology. The SEM of the as-synthesized material evidenced more uniform large crystals than those obtained in Example 2, with an average size of about 3 microns, as shown in FIG. 5. The as-synthesized ZSM-5 crystals exhibited a $SiO_2/Al_2O_3$ molar ratio of about 33.6.

Example 6

A mixture was prepared from ~955 grams of water, ~273 grams of Sipernat®-120, ~40 grams of sodium aluminate solution (45% in water), ~89 grams of triethanolamine (TEA) solution (98%), and ~75 grams of 50% aqueous sodium hydroxide solution. Then ~9 grams of ZSM-5 seeds were added to the mixture. The mixture exhibited the following molar composition:

| | |
|---|---|
| $SiO_2/Al_2O_3$ | ~40 |
| $H_2O/SiO_2$ | ~13.9 |
| $OH^-/SiO_2$ | ~0.2 |
| $Na^+/SiO_2$ | ~0.27 |

Figure 6:
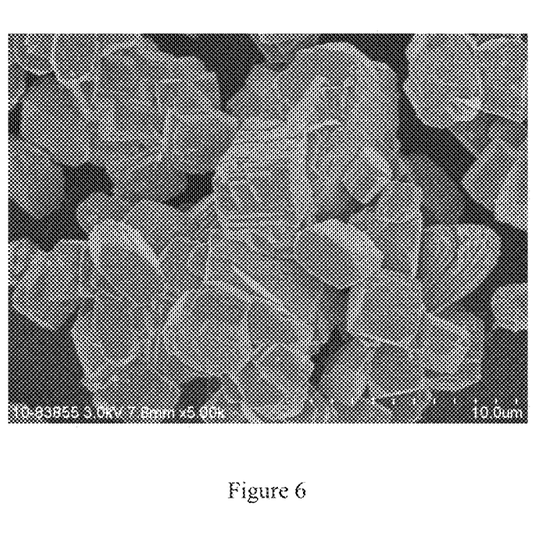
FIG. 6 provides an SEM image of the product of Example 6.

The reaction mixture was heated to about 320° F. (about 160° C.) in a ~2-autoclave with stirring at approximately 250 rpm for about 36 hours. The product was filtered, washed with deionized (DI) water, and dried at ~250° F. (~120° C.). The XRD pattern of the as-synthesized material showed the typical phase of ZSM-5 topology. The SEM of the as-synthesized material evidenced more uniform large crystals than those obtained in Example 2, with an average size of about 3 microns, as shown in FIG. 6. The as-synthesized ZSM-5 crystals exhibited a $SiO_2/Al_2O_3$ molar ratio of about 28.

Example 7

About 65 parts (basis: calcined at ~538° C.) of ZSM-5 crystal of Example 5 were mixed with about 35 parts of a regular Ultrasil™ silica mixture in a Lancaster mixer. Sufficient water was added to produce an extrudable paste on a ~2" Bonnot extruder. The mix of Example 5 ZSM-5, silica, and water-containing paste was extruded and dried in a hotpack overt at ~121° C. overnight (~8-16 hours). Crush strength of the resulting extrudates was observed to be about 125 lb/in. The dried extrudate was calcined in nitrogen at ~538° C. to convert the product to the calcined Na form. The $N_2$-calcined extrudate was humifidied with saturated air and exchanged with ~1N aqueous ammonium nitrate to remove sodium to a level below about 500 ppm. After ammonium nitrate exchange, the extrudate was washed with deionized water to remove residual nitrate ions prior to drying. The ammonium exchanged extrudate was dried at ~121° C. overnight (~8-16 hours) and calcined in air at ~538° C. After air calcination, the H-form extrudate exhibited an Alpha value of about 620.

While the invention has been described in detail with particular reference to certain preferred embodiments thereof, it will be understood that variations and modifications can be effected within the spirit and scope of the invention, which is limited only by the appended claims and equivalents thereof.

What is claimed is:

1. A process for preparing a high activity, large crystal ZSM-5 type zeolite in the absence of a template, the process comprising:
   (a) preparing a reaction mixture comprising water, a silica source having a surface area less than 150 $m^2/g$, an alumina source, seeds, a source of an oxide of an alkali metal, M, and a source of gluconic acid or salt thereof, Q, wherein said mixture has a $SiO_2/Al_2O_3$ molar ratio less than or equal to 40;
   (b) heating the reaction mixture at a crystallization temperature from about 100° C. to 200° C. for a time sufficient for crystals of ZSM-5 to form; and
   (c) recovering from the reaction mixture crystals of ZSM-5 having a $SiO_2/Al_2O_3$ molar ratio less than or equal to 40, wherein a majority of the crystals have at least one crystalline dimension of at least about 2 µm.

2. The process of claim 1, wherein the silica source has a specific surface area less than 125 $m^2/g$.

3. The process of claim 2, wherein the reaction mixture has a $SiO_2/Al_2O_3$ molar ratio from about 15/1 to about 40/1.

4. The process of claim 1, wherein the reaction mixture has a molar composition in the following amounts:
   $SiO_2/Al_2O_3$: up to about 40/1;
   $H_2O/SiO_2$: about 5 to about 50;
   $OH^-/SiO_2$: about 0.05 to about 0.5
   $M/SiO_2$; about 0.05 to about 0.5; and
   $Q/SiO_2$: about 0.05 to about 1.0.

5. The process of claim 1, herein heating step (b) is conducted for a time of about 2 hours to about 100 hours.

6. The process of claim 1, wherein the reaction mixture contains ZSM-5 seeds from a previous synthesis.

7. The process of claim 1, wherein the reaction mixture has a viscosity at 25° C. of less than 1000 cP.

8. The process of claim 1, wherein the ZSM-5 recovered in step (c) has a $SiO_2/Al_2O_3$ molar ratio less than or equal to 35.

* * * * *